United States Patent [19]

Kleiner et al.

[11] Patent Number: 5,693,842
[45] Date of Patent: Dec. 2, 1997

[54] PROCESS FOR PREPARING PHOSPHORUS-CONTAINING DICARBOXYLIC ACIDS ALKYL ESTERS THEREOF

[75] Inventors: Hans-Jerg Kleiner, Kronberg; Volker Freudenberger, Hofheim; Peter Klein, Wiesbaden, all of Germany

[73] Assignee: Hoechst AG, Frankfurt, Germany

[21] Appl. No.: 711,736

[22] Filed: Sep. 5, 1996

Related U.S. Application Data

[63] Continuation of Ser. No. 378,527, Jan. 26, 1995, abandoned.

[30] Foreign Application Priority Data

Jan. 29, 1994 [DE] Germany .................. 44 02 710.9

[51] Int. Cl.$^6$ .................................................. C07F 9/02
[52] U.S. Cl. .................. 558/82; 558/87; 568/11; 568/14; 568/15
[58] Field of Search .................. 558/82, 87; 568/11, 568/14, 15

[56] References Cited

FOREIGN PATENT DOCUMENTS

| 2646218 | 4/1977 | Germany . |
| 28 16 100 | 10/1978 | Germany . |
| 52-144627 | 12/1977 | Japan . |
| 1 575 157 | 9/1980 | United Kingdom ............. C07F 9/30 |

OTHER PUBLICATIONS

Chemical Abstracts, Abstract No. 088714, vol. 75, No. 13, "Phosphinic and phosphinous acid derivatives..."(Sep./1971).

Journal of the American Chemical Society, vol. 78, "Disubstituted Phosphine Oxides. III. Addition to alpha, beta–Unsaturated Nitriles and Carbonyl Compounds", pp. 5299–5303 (1956).

Chemical Abstracts, Abstract No. 059359, vol. 121, No. 6, "Epoxy resin–based thermosetting resin films..."(Mar./1994).

Kleiner, H–J, *Liebigs Ann. Chem. 1974*: 751–764.

Primary Examiner—José G. Deej
Assistant Examiner—Laura R. Cross
Attorney, Agent, or Firm—Connolly & Hutz

[57] ABSTRACT

The invention relates to a process for preparing phosphorus-containing compounds of the formula I

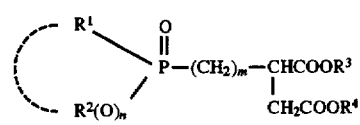

(I)

in which $R^1$ and $R^2$ are an alkyl radical having 1 to 8 carbon atoms, a cyclohexyl radical, a cyclopentyl radical, an aryl radical or a halogen-, alkyl- or alkoxy-substituted aryl radical, where $R^1$ and $R^2$ together with the phosphorus atom can also form a ring, n and m=0 or 1 and $R^3$ and $R^4$ are alkyl radicals having 1 to 4 carbon atoms or n=0, m=0 or 1 and $R^3$ and $R^4$ are H, by adding compounds of the formula II

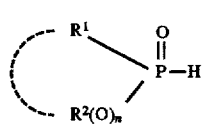

(II)

into dialkyl esters of fumaric acid or of maleic acid of the formula (III) or dialkyl esters of itaconic acid of the formula (IV)

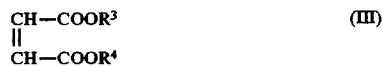

(III)

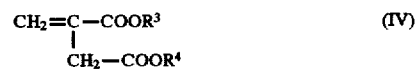

(IV)

in which $R^3$ and $R^4$ have the meaning given above, and, optionally reacting an alkyl ester of a phosphorus-containing dicarboxylic acid of the formula (I), where n=0, with water in the presence of catalytic amounts of an acid to give the phosphorus-containing dicarboxylic acid.

9 Claims, No Drawings

PROCESS FOR PREPARING PHOSPHORUS-CONTAINING DICARBOXYLIC ACIDS ALKYL ESTERS THEREOF

This is a continuation of U.S. application Ser. No. 08/378,527 filed Jan. 26, 1995, now abandoned.

The invention relates to a process for preparing phosphorus-containing dicarboxylic acids and alkyl esters thereof.

Alkyl esters of phosphorus-containing dicarboxylic acids are valuable comonomers and intermediates for preparing phosphorus-containing dicarboxylic acids which themselves can be used as monomers. These products are highly valuable in particular for use in preparing polyesters having low-flammability properties (see in this connection: DE-C 2646218, JP-A2-52/144,627, German Patent Application No. P 43 28 800.6).

The alkyl esters of phosphorus-containing dicarboxylic acids are obtained by addition of P(O)—H compounds to alkyl esters of unsaturated dicarboxylic acids. The addition can be performed with the aid of catalysts such as sodium methylate (DE-C 2646218, JP-A2-52/144,627). However, with regard to industrial use of these products, a preparation process without the use of catalysts is to be preferred. Such a preparation method comprises mixing the components and heating them over several hours at 100°–150° C. (Liebigs Ann. Chem. 1974, 751–764). It is a disadvantage of this process that numerous P(O)—H compounds decompose under this thermal stress and for safety reasons thus cannot be used for this reaction. In addition, the yields are not yet optimal.

There was therefore the requirement to develop a process which avoids the abovementioned disadvantages, which may be realised industrially without great expense and, furthermore, makes the desired products accessible in high yield and also in high purity.

This object is achieved by a process for preparing phosphorus-containing compounds of the formula (I)

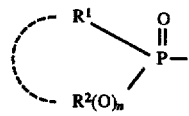

in which $R^1$ and $R^2$ are identical or different and are a straight-chain or branched alkyl radical having 1 to 8 carbon atoms, a cyclohexyl radical, a cyclopentyl radical, an aryl radical or a halogen-, alkyl- or alkoxy-substituted aryl radical, where $R^1$ and $R^2$ together with the phosphorus atom can also form a ring, in particular an oxaphosphorine ring, n and m=0 or 1 and $R^3$ and $R^4$ are alkyl radicals having 1 to 4 carbon atoms or n=0, m=0 or 1 and $R^3$ and $R^4$ are H, which comprises adding compounds of the formula II

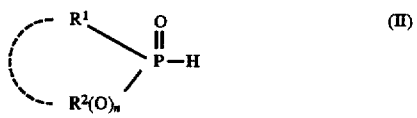

in which $R^1$ and $R^2$ and n have the meaning given above, into dialkyl esters of fumaric acid or of maleic acid of the formula (III) or dialkyl esters of itaconic acid of the formula (IV)

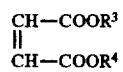

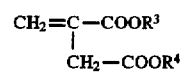

in which $R^3$ and $R^4$ have the meaning given above, and, if required, reacting an alkyl ester of a phosphorus-containing dicarboxylic acid of the formula (I), where n=0, with water in the presence of catalytic amounts of an acid to give the phosphorus-containing dicarboxylic acid.

The process is of particular interest for preparing compounds of the formula (I) in which $R^1$ and $R^2$ together with the phosphorus atom form an oxaphosphorine ring of the formula (V)

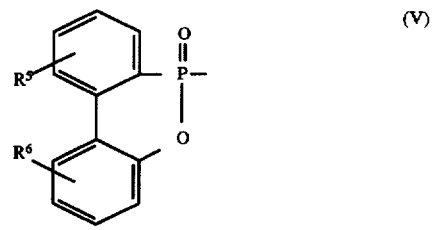

in which $R^5$ and $R^6$ are halogen, alkyl or alkoxy groups.

The process is also important for converting secondary phosphine oxides. Examples mentioned here are, e.g., dimethylphosphine oxide, methylethylphosphine oxide, dipropylphosphine oxide, diisopropylphosphine oxide, di-n-butylphosphine oxide, dicyclohexylphosphine oxide, methylphenylphosphine oxide, diphenylphosphine oxide, di-p-tolylphosphine oxide.

In addition, the use of 6H-dibenz[c,e]-1,2-oxaphosphorin-6-one is of importance.

The process is carried out in such a way that at 70°–180° C., in particular 90°–170° C., preferably 100°–160° C., under an inert gas atmosphere, the starting materials of the formula (II) are added to a dialkyl ester of fumaric acid or of maleic acid or to a dialkyl ester of itaconic acid. The addition is carried out over a period of 0.5 to 5 hours. The mixture is advantageously further stirred for one to ten hours at the reaction temperature. If these starting materials have low melting points in the range from about 30° to 50° C., they can alternatively preferably be added dropwise as a melt. The yields are very good. A purification, if required, can be carried out, e.g., by the known processes of distillation or crystallization. The process of the present invention can if required also be carried out continuously. The compounds of the formula (I) arising in pure form can, e.g., be used as comonomers in the preparation of flame-resistant polyesters.

Compounds of the formula (I) where n=0 in addition also serve as intermediates for preparing the corresponding dicarboxylic acids (VI) by hydrolysis. This hydrolysis is expediently carried out with water at 100°–150° C. in the presence of catalytic amounts of an acid, for example hydrochloric acid.

The hydrolysis proceeds according to the following formula:

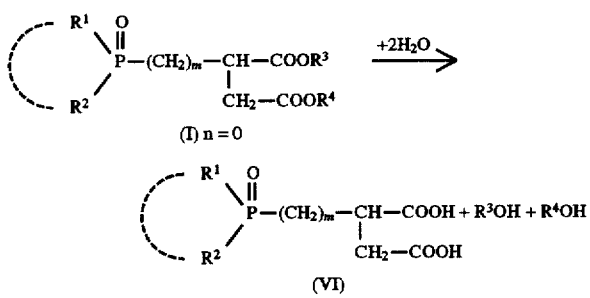

(I) n = 0

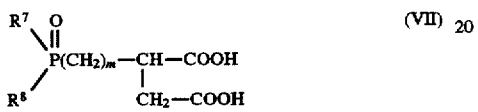

(VI)

The dicarboxylic acids (VI) are purified by conventional crystallization methods. They preferably serve as comonomers for preparing flame-resistant polyesters.

Of the dicarboxylic acids thus obtained, of particular interest are the compounds of the formula (VII)

$$\begin{array}{c} R^7 \\ \diagdown \parallel \\ \diagup P(CH_2)_m-CH-COOH \\ R^8 \quad\quad\quad | \\ \quad\quad\quad CH_2-COOH \end{array} \quad (VII)$$

in which $R^7$ and $R^8$ are identical or different and are a straight-chain or branched alkyl radical having 1 to 8 carbon atoms, the cyclohexyl radical, the cyclopentyl radical, an aryl radical or a halogen-, alkyl- or alkoxy-substituted aryl radical and m=0 or 1.

The compounds diphenylphosphinylmethylsuccinic acid, diphenylphosphinylsuccinic acid, dimethylphosphinylmethylsuccinic acid, dimethylphosphinylsuccinic acid, dibutylphosphinylmethylsuccinic acid, dibutylphosphinylsuccinic acid, dicyclohexylphosphinylmethylsuccinic acid and dicyclohexylphosphinylsuccinic acid are also of particular interest.

It is a particularly advantageous feature of the process according to the invention that the thermolabile P(O)—H compounds are exposed only very briefly to a thermal stress, since after addition they generally react quickly. The process can therefore also be carried out on an industrial scale without safety problems. It is particularly surprising here that in this process no telomerization according to

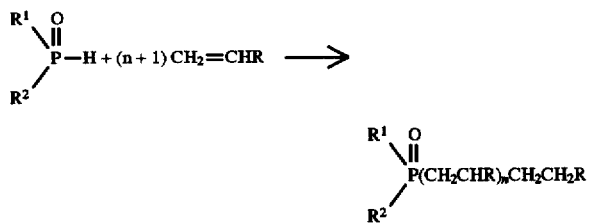

occurs which would actually be expected with the high excess of olefin (see in this context "Topics in Phosphorus Chemistry", Vol. 3, pages 10–11, John Wiley & Sons 1966).

Furthermore, it is surprising precisely with respect thereto that the yields in the process according to the invention generally exceed the yields of known processes.

EXAMPLE 1

126.4 g (0.8 mol) of dimethyl itaconate are heated under a nitrogen atmosphere to 150° C. and 62.4 g (0.8 mol) of dimethylphosphine oxide, which are kept liquid at 45° C., are added dropwise under vigorous stirring in the course of one hour. The mixture is then kept for three hours at 150°–155° C. It is then cooled and distilled at 0.7 mbar until an internal temperature of 165° C. is reached. After cooling, 179 g of crystalline residue are obtained having a melting point of 78°–82° C. This corresponds to a yield of 95% of theory. Crystallization from ethyl acetate gives the product with a melting point of 89°–91° C., boiling point: 167° C.; 0.5 mbar.

$C_9H_{17}O_5P$ (236)

calculated: 45.76% C 7.20% H 13.16% P found: 45.7% C 7.09% H 13.2% P

The dimethyl ester of diisopropylphosphinylmethylsuccinic acid was prepared in the same way (purification by a thin layer evaporator at a bath temperature of 205° C. (0.5 mbar))

$C_{13}H_{25}O_5P$ (292)

calculated: 53.43% C 8.56% H 10.62% P found: 53.3% C 8.42% H 10.7% P

EXAMPLE 2

36 g (0.25 mol) of dimethyl fumarate are heated under a nitrogen atmosphere to 150° C. and 19.5 g (0.25 mol) of dimethylphosphine oxide are added dropwise with vigorous stirring in the course of 50 minutes from a dropping funnel heated to 45° C. The mixture is then stirred for a further three hours at 140°–150° C. and cooled. It is then distilled at 0.5 mbar up to an internal temperature of 155° C. 53 g remain having a melting point of 44°–48° C. This corresponds to a yield of 95% of theory. Fine purification can be achieved by distillation (boiling point: 138°–140° C. at 0.2 mbar).

$C_8H_{15}O_5P$ (222)

calculated: 43.24% C 6.76% H 13.96% P found: 43.1% C 6.71% H 13.4% P

EXAMPLE 3

197.5 g (1.25 mol) of dimethyl itaconate are heated under a nitrogen atmosphere to 150° C. and 252.5 g (1.25 mol) of diphenylphosphine oxide were added dropwise in the course of one hour with vigorous stirring from a dropping funnel heated to 60° C. The mixture is then stirred for a further three hours at 140°–155° C. and then distilled at 0.5 mbar up to an internal temperature of 155° C. It is then cooled to 90° C. and 1 l of toluene are added. After cooling and crystallization, 380 g are obtained having a melting point of 80°–85° C. This corresponds to a yield of 85% of theory. Recrystallization again from toluene gives a product having a melting point of 91°–93° C.

$C_{19}H_{21}O_5P$ (360)

calculated: 63.33% C 5.83% H 8.61% P found: 63.1% C 5.91% H 8.4% P

EXAMPLE 4

180 g (1.25 mol) of dimethyl fumarate are heated under a nitrogen atmosphere to 150° C. and 252.5 g (1.25 mol) of diphenylphosphine oxide are added dropwise in the course of one hour with vigorous stirring from a dropping funnel heated to 60° C. The mixture is then stirred for a further 90 minutes at 150° C. It is then allowed to cool. After crystallization, 432.5 g are obtained having a melting point of 127°–129° C. This corresponds to a yield of 100% of theory. Recrystallization from ethyl acetate gives a melting point of 131°–133° C.

$C_{18}H_{19}O_5P$ (346)
calculated: 62.43% C 5.49% H 8.96% P
found: 62.4% C 5.41% H 8.7% P

EXAMPLE 5

39.5 g (0.25 mol) of dimethyl itaconate are heated under a nitrogen atmosphere to 150° C. and 54 g (0.25 mol) of 6H-dibenz[c,e]-1,2-oxaphosphorin-6-one are added in the course of 40 minutes. The mixture is then stirred for a further 8 hours at 140°–150° C. It is then distilled. At an overhead temperature of 267°–275° C. at 0.6–1.3 mbar, 70 g are obtained. This corresponds to a yield of 75% of theory. The product can be brought to crystallization by digestion with toluene, melting point: 94°–96° C.

EXAMPLE 6 a) Hydrolysis of the dimethyl dimethylphosphinylmethyl-succinate prepared according to Example 1.

80 g (0.34 mol) of dimethyl dimethylphosphinylmethyl-succinate are heated to reflux with a few drops of concentrated hydrochloric acid and 80 ml of water. Methanol slowly distils over a 70 cm silvered shell Vigreux column and at the same time a further 20 g of water are added dropwise. When the reaction is completed, the batch crystallizes. After addition of isopropanol, the mixture is stirred for several hours then filtered off by suction and dried. 65 g of dimethylphosphinylmethylsuccinic acid are obtained having a melting point of 139°–141° C. This corresponds to a yield of 92% of theory.

$C_7H_{13}O_5P$ (208)
calculated: 40.39% C 6.25% H 14.90% P
found: 40.1% C 6.1% H 14.5% P b) The diisopropyl compound was prepared in the same way, melting point: 144°–150° C.

$C_{11}H_{21}O_5P$ (264)
calculated: 50.0% C 7.96% H 11.74% P
found: 49.9% C 7.89% H 11.4% P c) The dimethyl ester of dimethylphosphinylsuccinic acid prepared according to Example 2 is hydrolyzed in the same manner as under 6 a). Dimethylphosphinylsuccinic acid is obtained in a 95% yield having a melting point of 174°–177° C.

$C_6H_{11}O_5P$ (194)
calculated: 37.11.% C 5.67% H 15.98% P
found: 37.05% C 5.7% H 16.0% P

We claim:

1. A process for preparing phosphorus-containing compounds of the formula I

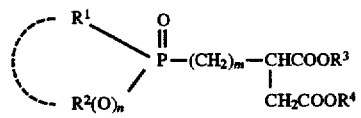

in which $R^1$ and $R^2$ are identical or different and are a straight-chain or branched alkyl radical having 1 to 8 carbon atoms, a cyclohexyl radical, a cyclopentyl radical, an aryl radical or a halogen-, alkyl- or alkoxy-substituted aryl radical, where $R^1$ and $R^2$ together with the phosphorus atom may also form a ring, n and m=0 or 1 and $R^3$ and $R^4$ are alkyl radicals having 1 to 4 carbon atoms or n=0, m=0 or 1 and $R^3$ and $R^4$ are H, which comprises adding at a temperature of 70° to 180° C. compounds of the formula II

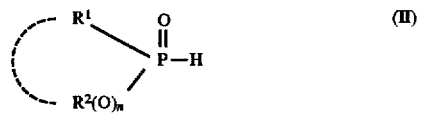

in which $R^1$ and $R^2$ and n having the meaning given above, into dialkyl esters of fumaric acid or maleic acid of the formula (III) or dialkyl esters of itaconic acid of the formula (IV)

in which $R^3$ and $R^4$ have the meaning given above, and, optionally reacting an alkyl ester of a phosphorus-containing dicarboxylic acid of the formula (I), where n=0, with water in the presence of catalytic amounts of an acid to give the phosphorus-containing dicarboxylic acid.

2. The process as claimed in claim 1, wherein $R^1$ and $R^2$ together with the phosphorus atom form an oxaphosphorine ring of the formula (V)

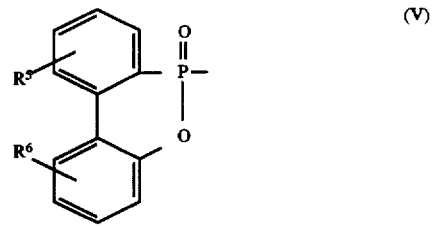

in which $R_5$ and $R^6$ are halogen, alkyl or alkoxy groups.

3. The process as claimed in claim 1, wherein the compounds of the formula (II) are secondary phosphine oxides.

4. The process as claimed in claim 1, wherein the addition is performed over a period of 0.5 to 5 hours.

5. The process as claimed in claim 3, wherein the compounds of formula (II) are selected from the group consisting of dimethylphosphine oxide, methylethylphosphine oxide, dipropylphosphine oxide, diisopropylphosphine oxide, di-n-butylphosphine oxide, dicyclohexylphosphine oxide, methylphenylphosphine oxide, and diphenylphosphine oxide of di-p-tolylphosphine oxide.

6. The process as claimed in claim 1, wherein the temperature is from 90° to 170° C.

7. The process as claimed in claim 1, wherein the temperature is from 100° to 160° C.

8. The process as claimed in claim 1, wherein the compound of formula (II) is 6H-dibenz(c,e)-1,2-oxaphosphonrin-6-one.

9. The process as claimed in claim 1, wherein $R^1$ and $R^2$ together with the phosphorus atom, form an oxaphosphorine ring.

* * * * *